(12) United States Patent
Marsh

(10) Patent No.: US 9,717,635 B2
(45) Date of Patent: Aug. 1, 2017

(54) ABSORBENT MEDICAL ACCESSORY

(71) Applicant: Savitri Marsh, Bay Shore, NY (US)

(72) Inventor: Savitri Marsh, Bay Shore, NY (US)

( * ) Notice: Subject to any disclaimer, the term of this patent is extended or adjusted under 35 U.S.C. 154(b) by 616 days.

(21) Appl. No.: 14/272,959

(22) Filed: May 8, 2014

(65) Prior Publication Data

US 2015/0320610 A1    Nov. 12, 2015

(51) Int. Cl.
| | |
|---|---|
| *A61M 1/00* | (2006.01) |
| *A61M 5/32* | (2006.01) |
| *A61F 15/00* | (2006.01) |
| *A61F 13/47* | (2006.01) |
| *A61F 13/534* | (2006.01) |
| *A61F 13/84* | (2006.01) |
| *A61F 13/539* | (2006.01) |
| *A61F 13/00* | (2006.01) |
| *A61F 13/02* | (2006.01) |
| *A61F 13/15* | (2006.01) |
| *A61F 13/45* | (2006.01) |

(52) U.S. Cl.
CPC ...... *A61F 15/008* (2013.01); *A61F 13/00068* (2013.01); *A61F 13/0203* (2013.01); *A61F 13/47* (2013.01); *A61F 13/534* (2013.01); *A61F 13/539* (2013.01); *A61F 13/84* (2013.01); *A61F 2013/00412* (2013.01); *A61F 2013/15008* (2013.01); *A61F 2013/4506* (2013.01); *A61F 2013/53908* (2013.01); *A61F 2013/8476* (2013.01); *A61F 2013/8488* (2013.01); *A61F 2013/8497* (2013.01)

(58) Field of Classification Search
CPC ........ A61F 13/84; A61F 13/47; A61F 13/534; A61F 13/539; A61F 2013/8476; A61F 2013/8488; A61F 2013/15008
USPC ........................... 604/385.01, 180, 179, 540
See application file for complete search history.

(56) References Cited

U.S. PATENT DOCUMENTS

| | | | |
|---|---|---|---|
| 3,422,817 A | 1/1969 | Mishkin et al. | |
| 4,327,716 A | 5/1982 | Ansted | |
| 4,891,846 A | 1/1990 | Sager et al. | |
| D313,653 S | 1/1991 | Ward et al. | |
| 5,968,000 A | 10/1999 | Harrison et al. | |
| 6,267,115 B1 | 7/2001 | Marshel | |
| 6,772,804 B1 | 8/2004 | Ryan | |
| 6,841,715 B2 * | 1/2005 | Roberts ................. | A61F 13/023 602/42 |
| 6,875,200 B1 | 4/2005 | Ajagbe | |
| D580,974 S | 11/2008 | Hammad | |

* cited by examiner

*Primary Examiner* — Jacqueline Stephens

(57) ABSTRACT

An absorbent medical accessory ensures that the skin around a medical tube remains dry. The accessory includes an upper pad having a top side, a bottom side and a perimeter edge extending between the top and bottom sides. The bottom side is comprised of an absorbent material. The upper pad has an opening extending through the top and bottom sides. A lower pad is coupled to the upper pad and has a top surface, a bottom surface and a peripheral edge extending between the top and bottom surfaces. The lower pad is comprised of an absorbent material. The lower pad has a hole extending through the top and bottom surfaces. The hole is alignable with the opening such that a medical tube is configured for being extended through each of the opening and the hole for retaining the medical tube against each of the upper and lower pads.

16 Claims, 2 Drawing Sheets

ABSORBENT MEDICAL ACCESSORY

BACKGROUND OF THE DISCLOSURE

Field of the Disclosure

The disclosure relates to medical accessories and more particularly pertains to a new medical accessory for ensuring that the skin around a medical tube, such as an enteral feeding tube or a tracheostomy tube, remains dry to help prevent irritation and inflammation of the person's skin.

SUMMARY OF THE DISCLOSURE

An embodiment of the disclosure meets the needs presented above by generally comprising an upper pad having a top side, a bottom side and a perimeter edge coupled to and extending between the top side and the bottom side. The bottom side is comprised of an absorbent material. The upper pad has an opening extending through the top side and bottom side. A lower pad has a top surface, a bottom surface and a peripheral edge coupled to and extending between the top surface and the bottom surface. The lower pad is comprised of an absorbent material. The lower pad is coupled to the upper pad. The lower pad has a hole extending through the top surface and the bottom surface. The hole is alignable with the opening such that a medical tube is configured for being extended through each of the opening and the hole for retaining the medical tube against each of the upper and lower pads.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
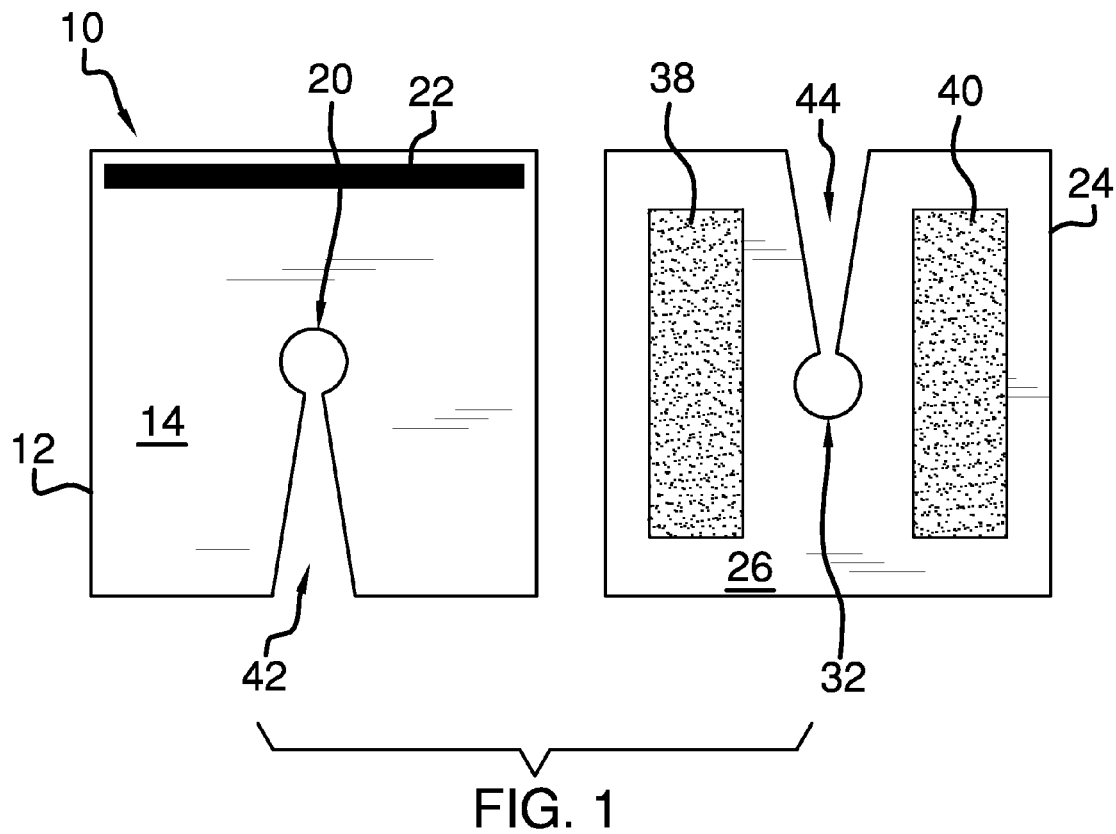
FIG. 1 is a top view of an absorbent medical accessory according to an embodiment of the disclosure.

With reference now to the drawings, and in particular to FIGS. 1 through 4 thereof, a new medical accessory embodying the principles and concepts of an embodiment of the disclosure and generally designated by the reference numeral 10 will be described.

As best illustrated in FIGS. 1 through 4, the absorbent medical accessory 10 generally comprises an upper pad 12 having a top side 14, a bottom side 16 and a perimeter edge 18 coupled to and extending between the top side 14 and the bottom side 16. The bottom side 16 is comprised of an absorbent material. The top side 14 may be comprised of a waterproof or water-resistant material. The upper pad 12 has an opening 20 extending through the top side 14 and the bottom side 14. The opening 20 may be annular or may have any other suitable shape. Marking indicia 22 is positioned on the top side 14 of the upper pad 12 for providing a visual distinction between the top side 14 and the bottom side 16 of the upper pad 12.

A lower pad 24 has a top surface 26, a bottom surface 28 and a peripheral edge 30 coupled to and extending between the top surface 26 and the bottom surface 28. The lower pad 24 is comprised of an absorbent material. The lower pad 24 is coupled to the upper pad 12. The lower pad 24 has a hole 32 extending through the top surface 26 and the bottom surface 28. The hole 32 and the opening 20 may have the same shape as each other. Thus, the hole 32 may also be annular. The hole 32 is alignable with the opening 20 such that a medical tube 34 is configured to be extended through each of the opening 20 and the hole 32 for retaining the medical tube 34 against each of the upper 12 and lower 24 pads. The medical tube 34 may include an enteral feeding tube, a tracheostomy tube or the like.

A coupler 36 removably couples the lower pad 24 and the upper pad 12. The coupler 36 may comprise a plurality of adhesive strips 38, 40. The coupler 36 is positioned on the top surface 26 of the lower pad 24 wherein the coupler 36 removably couples the top surface 26 of the lower pad 24 to the bottom side 16 of the upper pad 12. Each of the upper pad 12 and the lower pad 24 may be square-shaped and may have each of a length and a width between approximately 6.0 and 10.2 cm. The hole 32 and the opening 20 may each have a diameter between approximately 0.6 cm and 1.0 cm.

Figure 2:
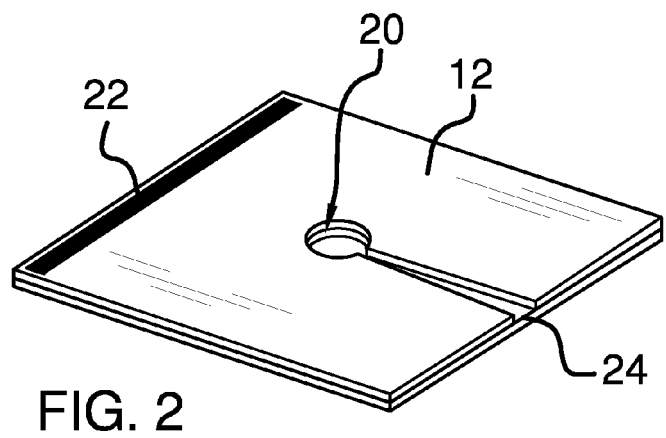
FIG. 2 is a top front side perspective view of an embodiment of the disclosure.
Figure 3:
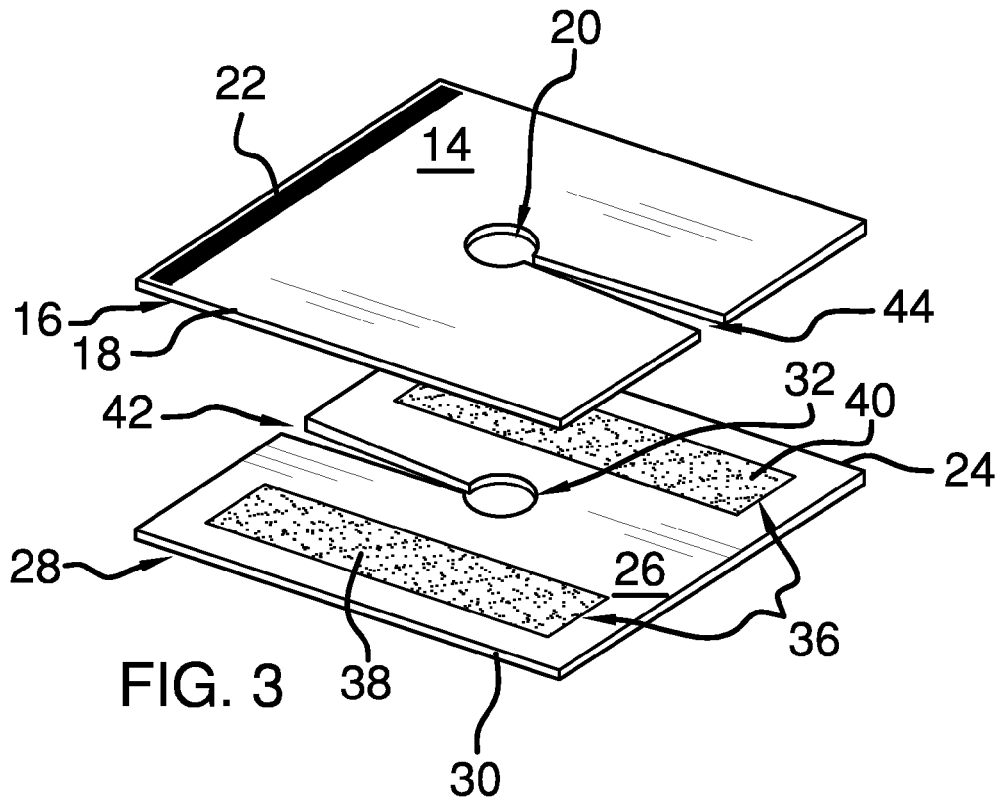
FIG. 3 is an exploded top front side perspective view of an embodiment of the disclosure.
Figure 4:
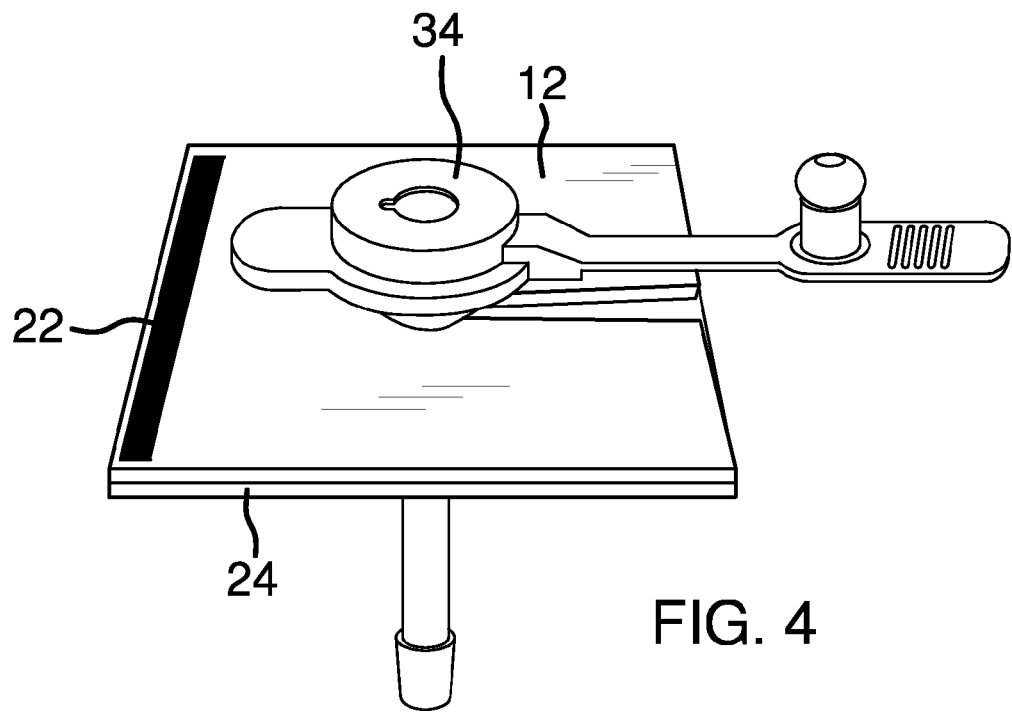
FIG. 4 is a top perspective view of an embodiment of the disclosure in use.

A slot 42 extends from the opening 20 through the perimeter edge 18. The slot 42 is configured to receive the medical tube 34 whereby the medical tube 34 is positionable in the opening 20. The slot 42 may taper outwardly from the opening 20 to the perimeter edge 18. Similarly, a slit 44 extends from the hole 32 through the peripheral edge 30. The slit 44 is configured to receive the medical tube 34 whereby the medical tube 34 is positionable in the hole 32. The slit 44 may taper outwardly from the hole 32 to the peripheral edge 30. The slit 44 and the slot 42 are parallel with respect to each other when the upper pad 12 is coupled to the lower pad 24. The slit 44 and the slot 42 may be spaced from each other when the upper pad 12 is coupled to the lower pad 24, as shown in FIGS. 2, 3 and 4. This orientation is useful when the medical tube 34 being used is an enteral feeding tube. In the event that a tracheostomy tube is being used for the medical tube 34, the slit 44 and the slot 42 may be positioned to overlap each other.

In use, as stated above and shown in the Figures, the lower pad 24 is positioned around the medical tube 34 such that the medical tube 34 extends through the hole 32. The medical tube 34 is also then inserted into the opening 20 in the upper pad 12. The upper pad 12 is attached to the lower pad 24 via the coupler 36 such that the coupler 36 secures the upper 12 and lower 24 pads together and holds them around the medical tube 34. In particular, the bottom surface 28 of the lower pad 24 is positioned against the person's body and the top side 14 of the upper pad 12 faces away from the person's body. When the medical tube 34 being used is a tracheostomy tube, the slit 44 and the slot 42 are positioned so that they overlap. Alternatively, when the medical tube 34 being used is an enteral feeding tube, the slit 44 and the slot 42 are parallel and positioned spaced from each other as best shown in FIG. 3. In this manner, the accessory 12 functions as a gauze for sealing the medical tube 34 and absorbing moisture to help keep the person's skin positioned adjacent to the medical tube 34 in a dry condition.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. An absorbent medical accessory comprising:
   an upper pad having a top side, a bottom side and a perimeter edge coupled to and extending between said top side and said bottom side, said bottom side being comprised of an absorbent material, said upper pad having an opening extending through said top side and said bottom side; and
   a lower pad having a top surface, a bottom surface and a peripheral edge coupled to and extending between said top surface and said bottom surface, said lower pad being comprised of an absorbent material, said lower pad being coupled to said upper pad, said lower pad having a hole extending through said top surface and said bottom surface, said hole being alignable with said opening such that a medical tube is configured for being extended through each of said opening and said hole for retaining the medical tube against each of said upper and lower pads; and
   a coupler removably coupling said lower pad and said upper pad.

2. The accessory of claim 1, further comprising said top side of said upper pad being comprised of a waterproof material.

3. The accessory of claim 2, further comprising marking indicia being positioned on said top side of said upper pad for providing a visual distinction between said top side and said bottom side of said upper pad.

4. The accessory of claim 1, further comprising wherein said coupler comprises a plurality of adhesive strips.

5. The accessory of claim 1, further comprising said coupler being positioned on said top surface of said lower pad wherein said coupler removably couples said top surface of said lower pad to said bottom side of said upper pad.

6. The accessory of claim 1, further comprising a slot extending from said opening through said perimeter edge, said slot being configured to receive the medical tube whereby the medical tube is positionable in said opening.

7. The accessory of claim 6, further comprising said slot tapering outwardly from said opening to said perimeter edge.

8. The accessory of claim 6, further comprising:
   a slit extending from said hole through said peripheral edge, said slit being configured to receive the medical tube whereby the medical tube is positionable in said hole; and
   said slit and said slot being parallel with respect to each other when said upper pad is coupled to said lower pad.

9. The accessory of claim 8, further comprising said slit and said slot being spaced from each other when said upper pad is coupled to said lower pad.

10. The accessory of claim 6, further comprising wherein said opening is annular.

11. The accessory of claim 1, further comprising a slit extending from said hole through said peripheral edge, said slit being configured to receive the medical tube whereby the medical tube is positionable in said hole.

12. The accessory of claim 11, further comprising said slit tapering outwardly from said hole to said peripheral edge.

13. The accessory of claim 11, further comprising wherein said hole is annular.

14. The accessory of claim 1, further comprising said opening and said hole having a same shape as each other.

15. An absorbent medical accessory comprising:
   an upper pad having a top side, a bottom side and a perimeter edge coupled to and extending between said top side and said bottom side, said bottom side being comprised of an absorbent material, said upper pad having an opening extending through said top side and said bottom side, said top side of said upper pad being comprised of a waterproof material;
   marking indicia being positioned on said top side of said upper pad for providing a visual distinction between said top side and said bottom side of said upper pad;
   a lower pad having a top surface, a bottom surface and a peripheral edge coupled to and extending between said top surface and said bottom surface, said lower pad being comprised of an absorbent material, said lower pad being coupled to said upper pad, said lower pad having a hole extending through said top surface and said bottom surface, said opening and said hole having a same shape as each other, said hole being alignable with said opening such that a medical tube is configured to be extended through each of said opening and said hole for retaining the medical tube against each of said upper and lower pads;
   a coupler removably coupling said lower pad and said upper pad, said coupler comprising a plurality of adhesive strips, said coupler being positioned on said top surface of said lower pad wherein said coupler removably couples said top surface of said lower pad to said bottom side of said upper pad;
   a slot extending from said opening through said perimeter edge, said slot being configured to receive the medical tube whereby the medical tube is positionable in said opening, said slot tapering outwardly from said opening to said perimeter edge; and
   a slit extending from said hole through said peripheral edge, said slit being configured to receive the medical tube whereby the medical tube is positionable in said hole, said slit tapering outwardly from said hole to said peripheral edge, said slit and said slot being parallel with respect to each other when said upper pad is coupled to said lower pad, said slit and said slot being spaced from each other when said upper pad is coupled to said lower pad.

16. An absorbent medical system comprising:

a medical tube;

an upper pad having a top side, a bottom side and a perimeter edge coupled to and extending between said top side and said bottom side, said bottom side being comprised of an absorbent material, said upper pad having an opening extending through said top side and said bottom side; and a lower pad having a top surface, a bottom surface and a peripheral edge coupled to and extending between said top surface and said bottom surface, said lower pad being comprised of an absorbent material, said lower pad being coupled to said upper pad, said lower pad having a hole extending through said top surface and said bottom surface, said hole being alignable with said opening such that said medical tube is extendable through each of said opening and said hole for retaining said medical tube against each of said upper and lower pads;

said top side of said upper pad being comprised of a waterproof material;

wherein said opening and said hole have a same shape as each other;

marking indicia being positioned on said top side of said upper pad for providing a visual distinction between said top side and said bottom side of said upper pad;

a coupler removably coupling said lower pad and said upper pad, said coupler comprising a plurality of adhesive strips, said coupler being positioned on said top surface of said lower pad wherein said coupler removably couples said top surface of said lower pad to said bottom side of said upper pad;

a slot extending from said opening through said perimeter edge, said slot receiving said medical tube whereby said medical tube is positionable in said opening, said slot tapering outwardly from said opening to said perimeter edge; and a slit extending from said hole through said peripheral edge, said slit receiving said medical tube whereby said medical tube is positionable in said hole, said slit tapering outwardly from said hole to said peripheral edge, said slit and said slot being parallel with respect to each other when said upper pad is coupled to said lower pad, said slit and said slot being spaced from each other when said upper pad is coupled to said lower pad.

* * * * *